US006833112B2

United States Patent
Hoummady (10) Patent No.: US 6,833,112 B2
(45) Date of Patent: Dec. 21, 2004

(54) HIGH PERFORMANCE SYSTEM FOR THE PARALLEL AND SELECTIVE DISPENSING OF MICRO-DROPLETS, AND TRANSPORTABLE CARTRIDGE AND DISPENSING KIT USING SAID SYSTEM

(76) Inventor: Moussa Hoummady, 16 B rue de Vesoul, Besancon (FR), 25000

(*) Notice: Subject to any disclaimer, the term of this patent is extended or adjusted under 35 U.S.C. 154(b) by 339 days.

(21) Appl. No.: 09/882,308

(22) Filed: Jun. 15, 2001

(65) Prior Publication Data

US 2002/0121529 A1 Sep. 5, 2002

(30) Foreign Application Priority Data

Jun. 15, 2000 (CA) .............................................. 2311622

(51) Int. Cl.⁷ .............................. G01N 1/10; B01L 3/02
(52) U.S. Cl. ............................. 422/61; 347/21; 347/40; 347/48; 347/68; 422/100; 436/86; 436/94; 436/180
(58) Field of Search ............................. 347/21, 40, 48, 347/68; 422/61, 100; 436/86, 94, 180

(56) References Cited

U.S. PATENT DOCUMENTS

| | | | | | |
|---|---|---|---|---|---|
| 3,958,255 | A | * | 5/1976 | Chiou et al. .................... | 347/47 |
| 4,014,029 | A | * | 3/1977 | Lane et al. ..................... | 347/47 |
| 4,475,113 | A | * | 10/1984 | Lee et al. ....................... | 347/47 |
| 4,680,595 | A | | 7/1987 | Cruz-Uribe et al. ........ | 346/140 |
| 4,730,196 | A | | 3/1988 | van Esdonk et al. ... | 346/140 R |
| 5,471,232 | A | * | 11/1995 | Hosono et al. ................ | 347/70 |
| 5,877,580 | A | * | 3/1999 | Swierkowski ................ | 310/328 |
| 6,010,208 | A | * | 1/2000 | Powers et al. ................. | 347/65 |
| 6,270,202 | B1 | * | 8/2001 | Namba et al. ................. | 347/68 |
| 6,402,971 | B2 | * | 6/2002 | Hashizume et al. .......... | 216/27 |

OTHER PUBLICATIONS

Ekström, S. et al, Analytical Chemistry 2000, 72, 286–293.*
Oennerfjord, P., et al., "Picoliter Sample Preparation In MALDI–TOF MS Using a Micromachined Silicon Flow–Through Dispenser" Analytical Chemistry, American Chemical society, Columbus, US, vol. 70, No. 22, Nov. 1998, pp. 4755–4760.
Blanchard, A. P., et al., "High–Density Oligonucleotide Arrays" Biosensors & Bioelectronics, Elsevier Science Publishers, Barking, GB, vol. 11, No. 6/7, Apr. 1996, pp. 687–690.

* cited by examiner

Primary Examiner—Arlen Soderquist
(74) Attorney, Agent, or Firm—Clark & Brody

(57) ABSTRACT

This invention aims at allowing a consistent increase in the output of selective dispensing of micro-droplets, at making a spatial, targeted selectivity by distributing a predetermined reagent on the predetermined site, and at creating a multi-functional system, easy to adjust.

An example of dispensing system according to this invention consists of a substrate (2) covered by a membrane (3) and of means for deforming (65) the membrane at the right of each cavity formed in the substrate, and where the cavities, etched in a material constituting the substrate (2) in a matrix shape, appear in the shape of wells (10) crossing the substrate with lateral, continuous walls (11) of axial symmetry; each well opening on the upper surface and the lower surface of the substrate with respectively a feeding opening (12) and an ejection duct (14), the feeding opening showing an opening consistently higher than the opening (13) of the duct.

Application to the manufacturing of cartridges and of miniaturised kits in biochemistry and pharmacy, or also in cosmetics, in analytical instrumentation, in printing by inkjet or in the automobile electronics.

16 Claims, 9 Drawing Sheets

HIGH PERFORMANCE SYSTEM FOR THE PARALLEL AND SELECTIVE DISPENSING OF MICRO-DROPLETS, AND TRANSPORTABLE CARTRIDGE AND DISPENSING KIT USING SAID SYSTEM

The invention concerns a high-performance system for parallel and selective dispensing of extremely small volume micro-droplets—of the order of a sub-multiple of nano-liter, even of a sub-multiple of pico-liter-, transportable cartridges and of a kit to put to practice such a dispensing, as well as the applications of this system, notably in chemistry, in biology, in biotechnology or pharmacy—in particular for the manufacturing of bio-chips, for pharmaceutical, immunological, or biochemical tests, for the screening of drug libraries or serum banks, for the preparation of drugs or their percutaneous administration by iontophoresis, or else in the fields of cosmetics, for the making of perfume atomisers or aerosol, in inkjet printing or in automobile electronics, specifically for gas or oil fuel injectors.

Recent research progress in genomics and proteomics have made available a considerable number of biological and therapeutical molecules for testing. Nevertheless, the low quantities of available biochemical products as well as their high cost have led to look for a sensible increase of experimentation abilities by performance optimisation.

In order to do so, various techniques have been used for handling biochemical liquids, such as colony transfer systems or micro-pipetting systems with piezoelectric actuators and, more recently, the inkjet printing technique.

The goal of these technologies is the manufacturing of bio-chips by dispensing biological probes (of oligonucleotides, proteins, peptides, etc.), pre-synthesised in the majority of cases, on a surface of different types of support, such as glass, nylon® or cellulose®.

Known for example from documents U.S. Pat. No. 5,053,100 or U.S. Pat. No. 6,083,762, are dispensers using a piezoelectric transducer on a micro-dispenser. This technique allows the application in situ of pre-synthesised or synthesised oligonucleotides. However, these systems are made by the unit and are unfit for high-density parallel dispensing.

In document U.S. Pat. No. 6,028,189, dispensing of reagents is done through the use of inkjet-type micro-pumps, activated by a piezoelectric actuator. Each micro-pump is built in a silicon bloc, with droplets feeding and ejecting channels. In order to obtain syntheses in situ, four micro-pumps deliver DNA bases by ejection in circular wells, formed on a glass substrate having its motion controlled along two axes.

These systems do not allow a high performance application according to the present invention, that is a few hundred to a few thousand of droplets by $cm^2$: with four pumps running at a few hundred of Hz, a machine according to the previous document would apply 100 000 droplets in a few hundred seconds. The synthesis of 25 oligonucleotides probes would then require more than 2 hours.

The invention aims at considerably increasing the performance of the selective dispensing of micro-droplets, through a strong increase of the density of parallel applications, comparable to the densities obtained by photochemistry for the stopping of specific molecules though photolithographic masks. This method is restricted to those molecules that can be fixed by photochemistry and it basically does not allow to handle the reagent droplets individually. Moreover, synthesis in situ, with this method, is restricted to about 25 mononucleotides.

Another objective of the invention is to allows a selectivity which is not only spatial, by distributing the reagent on predetermined or programmed sites, but also targeted, by distributing a selected one of a plurality of reagents on the predetermined site.

The invention also aims at creating a multifunctional system easy to adapt under different forms, for instance to biological and biochemical analysis miniature kits for enabling a great number of applications. In particular, the invention allows not to be restricted to the synthesis of 25 nucleotides per probe but to synthesise long probes reaching, for instance, 70 nucleotides, while keeping a high performance.

These objectives are met by using a dispensing head into which is made, through high density microelectronic-type techniques a matrix of wells of specific shape and fed according to a specific connection for a high-output selective dispensing.

More precisely, the object of the invention is a high-performance micro-droplets dispensing system, comprising a substrate covered by a membrane and means for deforming the membrane perpendicularly to each cavity formed in the substrate, and where the cavities, etched in a material forming the substrate, appear in the shape of wells crossing the substrate with a lateral continuous inner wall of axial symmetry; each well opens on the upper surface and the lower surface of the substrate as respectively a feeding opening and a duct opened as an ejection nozzle, the feeding opening presenting an opening higher than the nozzle of the duct, and the duct presenting a shape ratio between 1 to 20.

According to the invention, the expression "distributing" is to be understood as the ejection or the suction of micro-droplets, by high-output of some tens to some thousands of micro-droplets dispensed parallely in a split second, the expression "axial symmetry wall" as a revolution or cylindrical surface, for instance of a square cross-section, and the expression "shape ratio" as the ratio between the height and the opening of the exit duct.

To reach this type of performance, the substrate shows a well density which can reach 10 000 per $cm^2$, with a flow that can exceed 1 million droplets per second.

Advantageously, the substrate material is chosen among semiconducting materials such as silicon, gallium arsenide, silicon carbide, germanium, oxyde and insulating composites (such as SOI, initials for silicon-oxyde-insulator), glasses, silicon nitrides, polysilicon, ceramics, thermoplastic materials,—such as methyl polymethacrylate, polycarbonates, polytetrafluoroethylene, polyvinyle chloride or polydimethylsiloxane, thick photosensitive resins (for instance, the resin <<SUB >>)-, as well as metals, such as tungsten or stainless steels.

Preferably, Micro-manufacturing techniques to make the wells or the micro-channels are selected according to the material of the substrate:

wet or dry chemical etching such as reactive ion etching (RIE in short) or deep etching (D-RIE in short) for silicon and glass;

etching by spark-machining or electroforming for metals;

casting and polymerisation for thermoplastic materials;

photolithography, laser cutting, ultrasounds, or by abrasive projection for the majority of substrates.

According to preferred embodiments, the material of the membrane is selected among glass, silicon, elastomers and thermoplastics; the membrane may be etched using the above-mentioned etching techniques, in order to generate a network of well feeding micro-channels; these micro-channels are coupled at both ends to as least one feeding reagent tank.

According to particular embodiments, the means for locally deforming the membrane are embodied by electromagnetic, magnetostrictive or piezoelectric actuators. Alternative means are also considered such as thermal means of the inkjet type or thermoplastic by bimetallic type effect, the electro-vaporising generated by an electric field located between each well, or else electrostatic actuators.

All of the deforming means can be managed by a single command unit programmable through a multiplexing network. Such a unit allows to trigger simultaneously or successively the suction or the dispensing of identical or different reagents through all the wells, through blocs of wells or certain wells.

According to particular embodiments, the dispensing head has four or a multiple of four lines and a number of columns of wells adjusted to the required density, in order to carry out the synthesis of the DNA probes from the four basic nucleotides monomers for the production of bio-chips. The wells in each line are fed by the same reservoir through a micro-duct formed in the membrane parallely to the line of wells and coupled laterally to the line or orthogonally to the plane of the substrate, the reservoirs being etched in the membrane or placed at a distance and connected to the micro-ducts by flexible links.

The invention also concerns the applications of the dispensing head defined hereinabove. In order to implement at least some of them, it is more profitable to prepare a set ready for use in the form of:

dispensing cartridge including at least one dispensing head pre-filled with reagents and with titration plates of a semiconducting or thermoplastic material, that can show micro-bowls formed by etching of microelectronic type, by machining, by moulding, by thermoforming, or any techniques adjusted to such a production;

dispensing kit including at least one dispensing head, that can be equipped with at least an suction pump and at least one titration plate, pre-filled with reagent or not.

These cartridges or these kits are especially intended for the preparation of bio-chips, by in situ synthesis or deposit of pre-synthesised oligonucleotides, for the collective or individual screening of biological molecules or of cells, for the preparation of drugs or for pharmaceutical tests or for immunological, biochemical and biological screening.

The percutaneous administration of drugs by iontophoresis can be made from a dispensing head as previously defined consisting of several wells. A system for applying an adequate potential difference on a piezoelectrical cell, or any other electromagnetic actuating means, form an administration device of a calibrated quantity of at least one drug contained or formed in this well.

Besides the applications above mentioned, the invention can also be used for separation and sorting, for instance in chromatography by selective filtration. Identical or different bio-cells are first fixed, grafted, blocked or hanged, by any known means, on the walls of the wells of a dispensing head according to the invention, for each well or block of wells. The dispensing head can be integrated at the tip of a syringe.

Other characteristics, advantages, applications will also be apparent from the following description which details, in particular, some examples of non-restrictive embodiments of the present invention, with reference to the appended drawing which show respectively.

On all the figures, identical reference numbers indicate identical or technically equivalent elements. Membranes appear in transparency in order to facilitate the visualisation of the whole of the elements shown.

Figure 1:
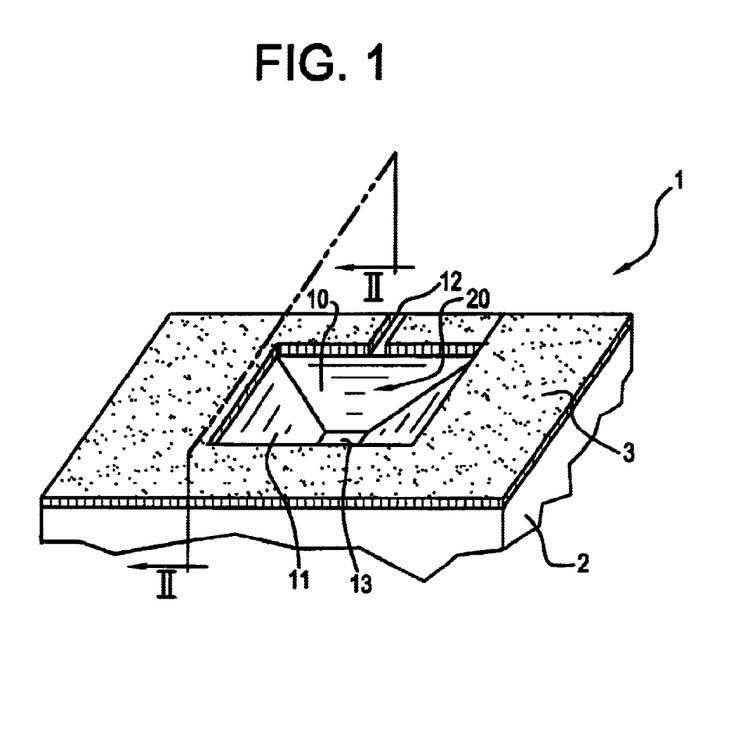
in FIG. 1, a perspective partial schematic view of a dispensing head limited to the environment of a basic well of a system according to the invention.

An example of dispensing head 1 is illustrated in FIG. 1, as limited to its environment around a dispensing well 10. Each well 10 was etched by photolithography followed by a wet chemical etching in a silicon substrate 2 covered by a pyrex® membrane 3, the membrane and the substrate being assembled by anodic welding to form head 1.

Well 10 has a reversed pyramidal shape, and crosses the silicon substrate 2 right through according to four continuously sloped walls 11 defined by crystal plane 1-1-1 of silicon. The upper opening 12 of the well, which communicates with membrane 3, form a square of greater size than the lower duct 13 in order to accelerate the ejection of the droplets. A micro-channel 20 for feeding reagents to or draining reagents from the well is machined in the membrane 3.

In this example of realisation, the well dimensions are the following:

side of the upper opening: 500 $\mu$m side of the lower duct: between 10 and 50 $\mu$m (about 30 $\mu$m)

membrane thickness: 10 to 50 $\mu$m substrate thickness: 360 $\mu$m

Figure 2:
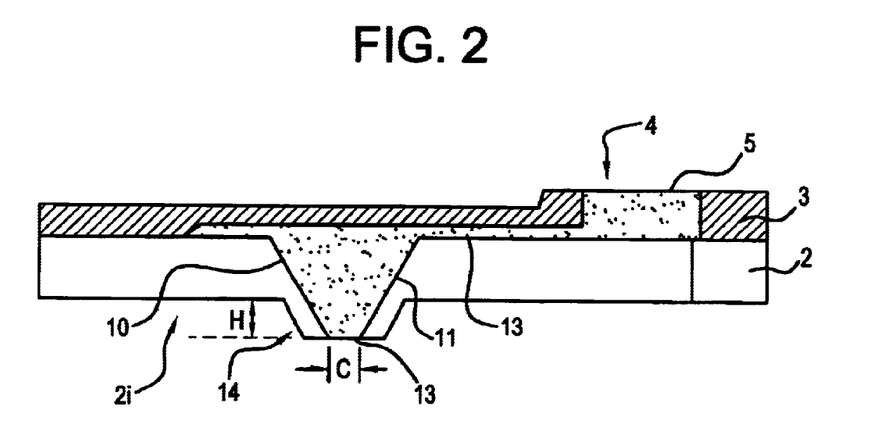
in FIG. 2, a cross section view according to II—II of the head in FIG. 1 with a filling reservoir.

In the cross section view of FIG. 2 according to II—II, it can be seen that micro-duct 13 communicates with a reagent feeding or stocking reservoir 4. It is also shown in this view that the generally flat lower surface 2i of substrate 2 projects around the lateral walls 11 of well 10 so as to extend these walls to form a duct 14. Such ducts are obtained by machining the lower surface. The height H of such a duct with respect to side C, the side of the opening 13, measures the shape ratio equal to about 3 in the example, which improves the formation of micro-droplets of volume of the order of a pico-liter. The value of the shape ratio is limited by technological constraints and a good compromise is to be looked for between 1 and 20, according to the material and the etching technique used. Moreover, the average distance between two wells is typically about 550 µm.

Figure 3:
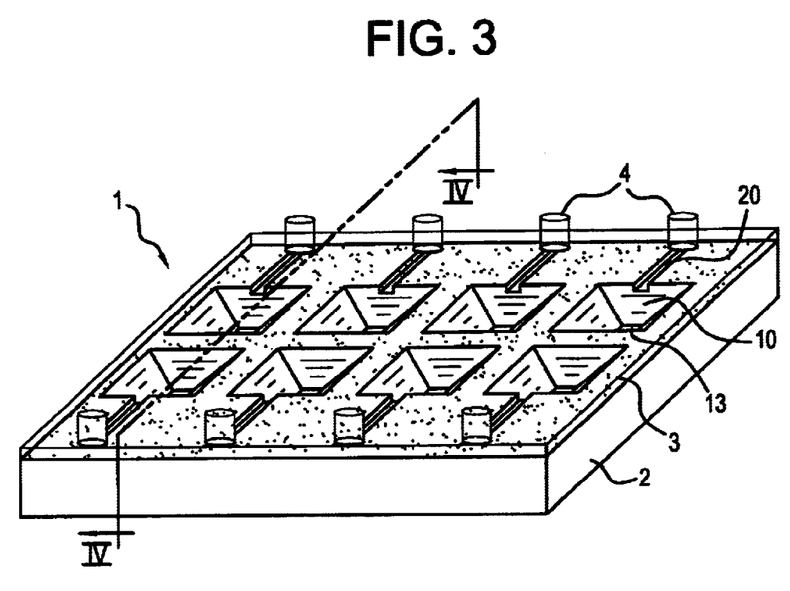
in FIG. 3, a perspective schematic view of a dispensing head of a system according to the invention having eight dispensing wells.
Figure 4:
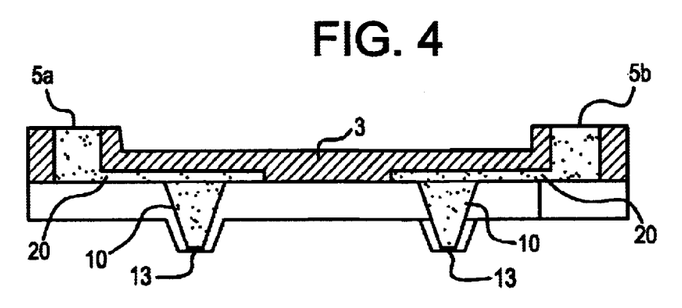
in FIG. 4, a cross section view according to IV—IV of the previous figure.

In FIG. 3, the perspective view of a dispensing head 1 is composed of eight wells 10 connected individually to eight reservoirs 4 by eight micro-ducts 20. Typical dimensions of such as head are:

length: 3 mm
width: 5 mm
thickness: 1 mm according to the thickness of the reservoirs The cross section view shown in FIG. 4, according to plane IV—IV of the previous figure, clearly shows the independence of the reservoirs 4 allowing the dispensing or the suction of different reagents 5a et 5b.

Figure 5:
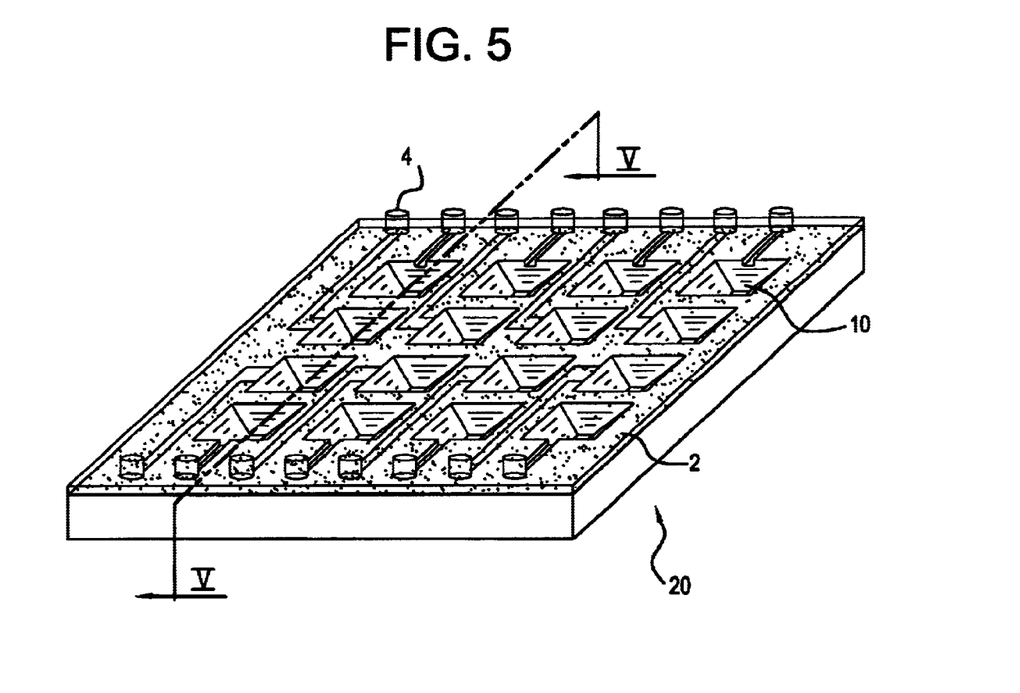
in FIG. 5, a perspective schematic view of a dispensing head of a system according to the invention having sixteen dispensing wells.
Figure 6:
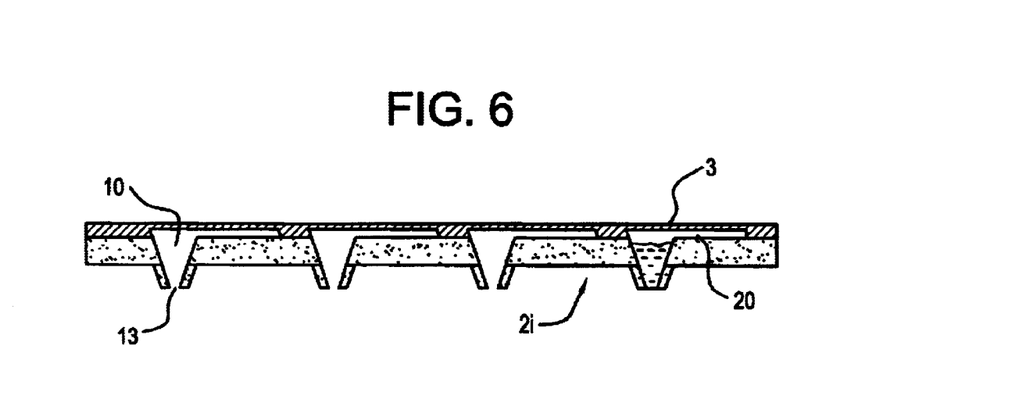
in FIG. 6, a cross-sectional view according to V—V of the previous figure.

As a variant, FIGS. 5 and 6 show, respectively a bird's eye view and a cross sections view according to plane V—V, a dispensing head composed of sixteen wells 10 individually connected to sixteen reservoirs 4 by sixteen micro-ducts 20. Such a configuration is advantageously used to dispense sixteen different reagents.

Figure 7:
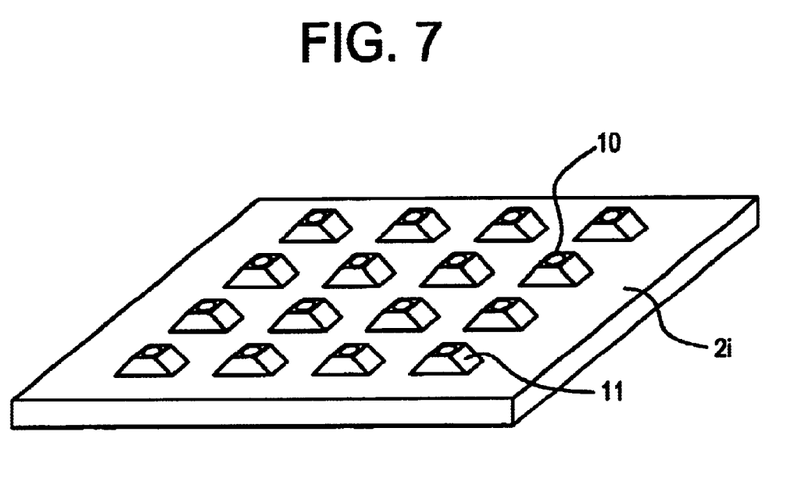
in FIGS. 7 and 8, two bird's eye views of the lower surface of the dispensing head of the system according to FIG. 5 and to a variant.
Figure 8:
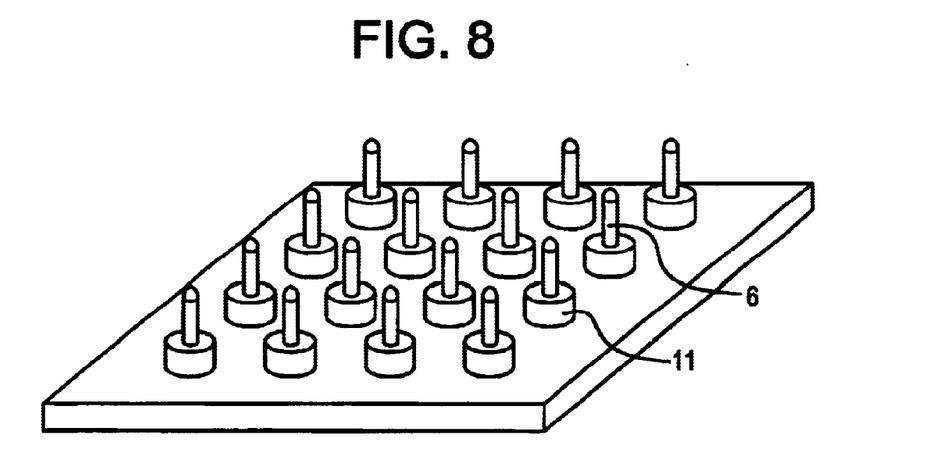

The generally flat lower surface 2i of the substrate 2 of the dispensing head of FIGS. 5 and 6, is shown in a bird's eye view in FIG. 7 and as a variation in FIG. 8. In FIG. 7, the walls of the wells 10 can be seen projecting in the shape of pyramids. This sloped shape of the sides is advantageous since it prevents the accumulation and therefore the stagnation of the reagent. Moreover, from an hydrodynamic point of view, it allows a better flow with a continuous distribution of pressures and speed. In FIG. 8, these same walls 11 are shown in transparency in a cylindrical shape, 100 microns in diameter, extended by a centred tip 6, having a cylindrical shape as well and 20 microns in diameter.

Figure 9:
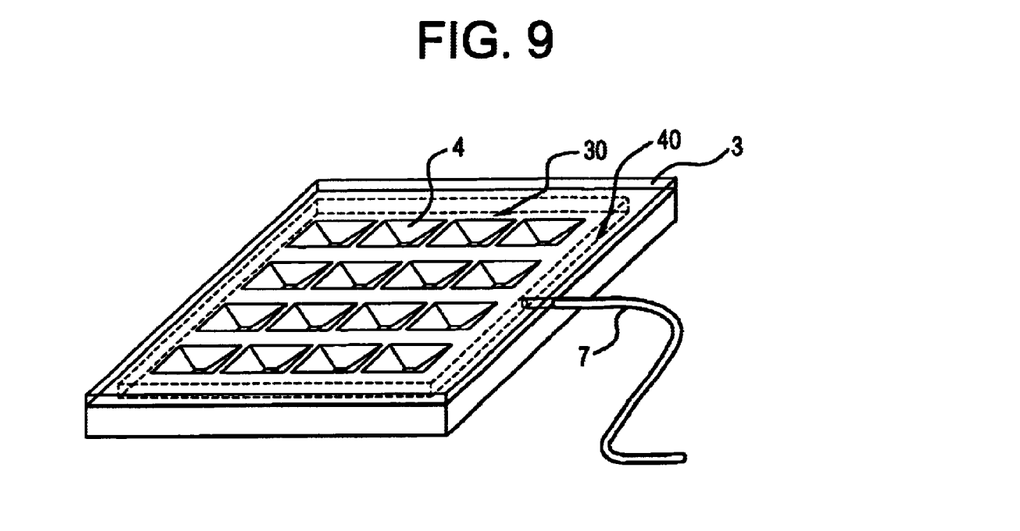
in FIG. 9, a perspective view of the system according to FIG. 5 with remote reagent dispensing means.

When a single reagent is dispensed or sucked simultaneously through the wells, the membrane configuration shown in FIG. 9 is advantageously put to use. In this configuration, the membrane 3 has a single opening 30 which allows to feed or to suck a same reagent on all wells 4 without using the micro-ducks. This reagent is transported from or is sucked towards a distant reservoir (not shown) through a flexible pipe 7 coupled with a single micro-capillary 40 crossing the membrane 3.

Figure 10:
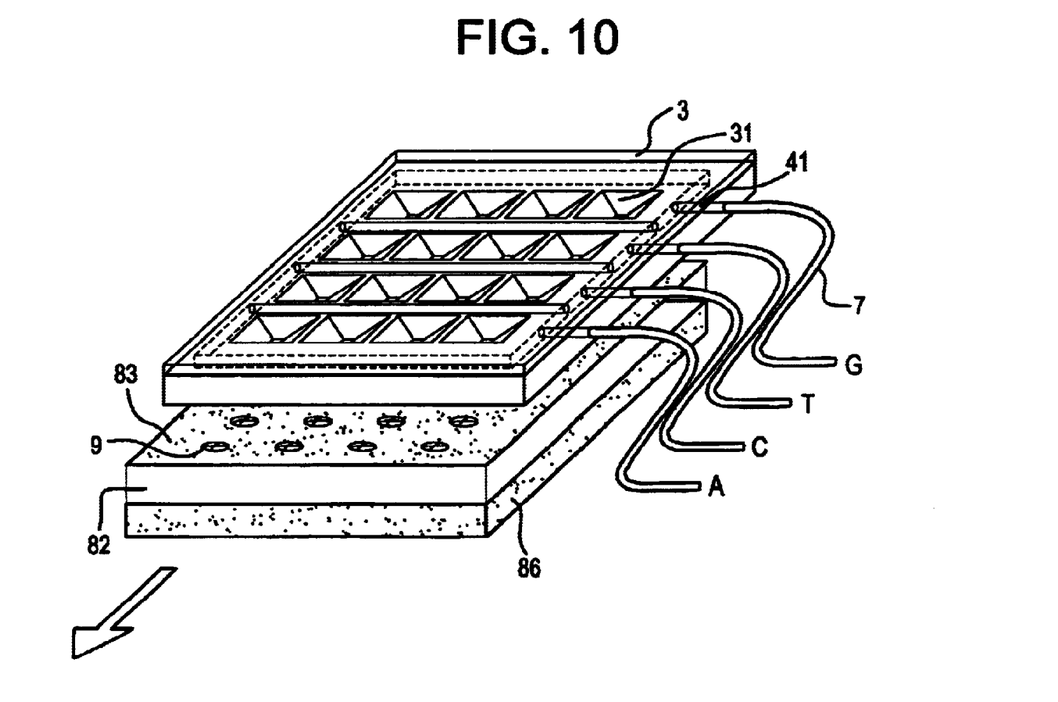
in FIG. 10, a perspective view of the system according to FIG. 5 with remote dispensing means for four mononucleides to form probes on a mobile plate.

When several reagents are dispensed, for instance four mononucleides A, C, T, G, in the case shown in the perspective view of FIG. 10, the above membrane is divided by three traverses 31 so as to form four independent reagent feeding or sucking canals 32. These canals are connected to four micro-capillaries 41 coupled, through membrane 3 and four flexible pipes 7, to four distant reservoirs (not shown). Such a configuration is particularly suited to the dispensing of the four basic nucleotides to form probes 9 for the preparation of micro-chips on a plate 82 covered by a layer of silicon compound 83 to allow the grafting of the first nucleides. Plate 82 is supported by a positioning device 86, according to axes XYZ.

Figure 11:
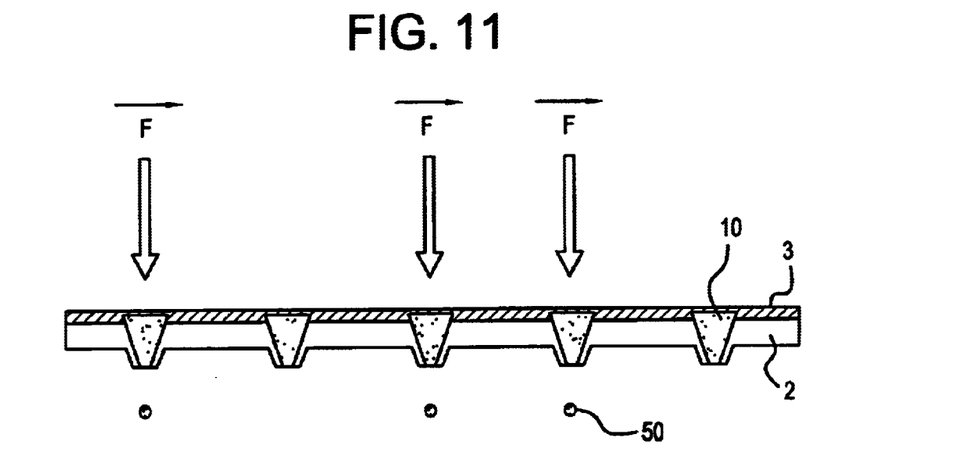
in FIG. 11, a cross-sectional schematic view of a dispensing system according to the invention illustrating the selective actuation principle of the dispensing wells.

In order to distribute the reagent(s) by micro-droplets 50 in a selective manner, that is by using each well independently of the others, membrane 3 is approached locally, as shown in the cross section view of FIG. 11. The selective actuating of the dispensing wells 10 is caused by means that locally deform membrane 3 by applying a force $\vec{F}$.

Figure 12A:
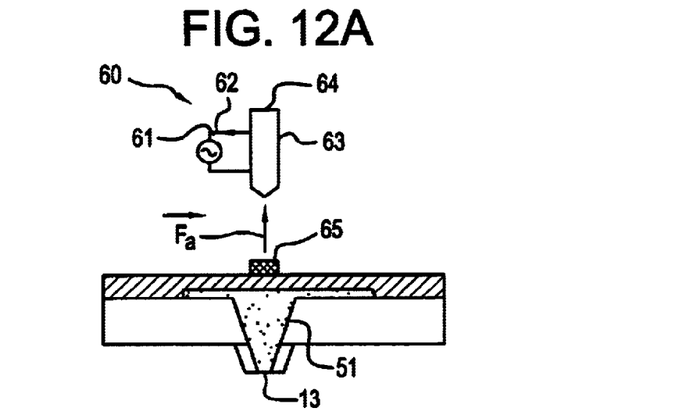
in FIGS. 12*a* and 12*b*, cross section views illustrating the two actuating phases of wells by electromagnetic selective actuation means.
Figure 12B:
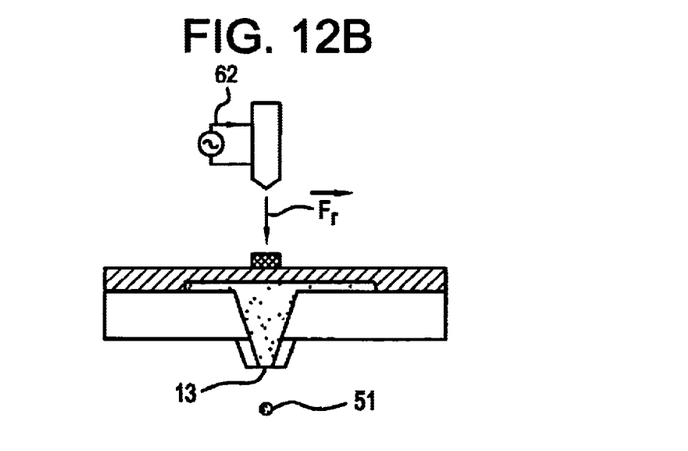

In the cross section views of FIGS. 12a and 12b, the two actuating phases of activation of a well 10 by locally deforming the membrane activated by the electromagnetic actuating means are shown. These means are embodied by an basic electromagnet 60 composed of an excitation circuit 61 which generates electric currant, including in particular a coil 63 coupled to an air-gap centre 64. The electromagnetic means also include a magnetic chip 65, fixed on membrane 3 perpendicularly to the well and able to be polarised by the electromagnet. The chip may alternatively be a permanent magnet, or made of diamagnetic or paramagnetic material.

When current 62 circulates, the centre 63 exerts an attractive force $\vec{F}_a$ on the chip 65. The membrane 3 is then deformed towards the electromagnet and the flow of liquid 51 is stopped at the opening 13 (FIG. 12a). When current 62 circulates in the other direction by inverting the poles, the centre 63 exerts a repulsive force $\vec{F}_r$ on the magnetic chip 65. The membrane is bent in a hollow shape and liquid 51 is ejected as micro-droplets 50 through opening 13 of the ejection duct (FIG. 12b), with a volume calibrated and controlled by the dimensions of the duct as well as by the amplitude and the duration of the applied electric signal.

Alternatively, the droplets ejection can be done by applying pulses of electric current or by applying an alternating current at the resonance frequency of the membrane.

Figure 13A:
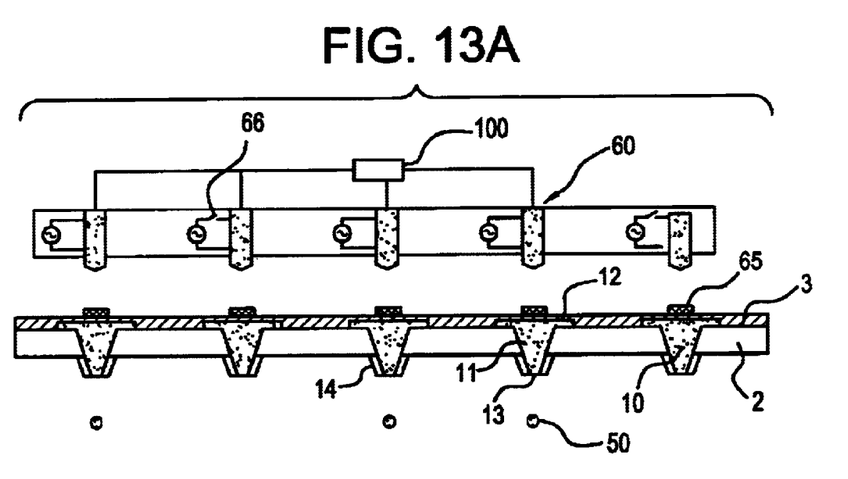
in FIGS. 13*a* and 13*b*, a cross section view of a dispensing system according to the invention, illustrating the selective activation respectively by electromagnetic and piezoelectric selective actuating means.
Figure 13B:
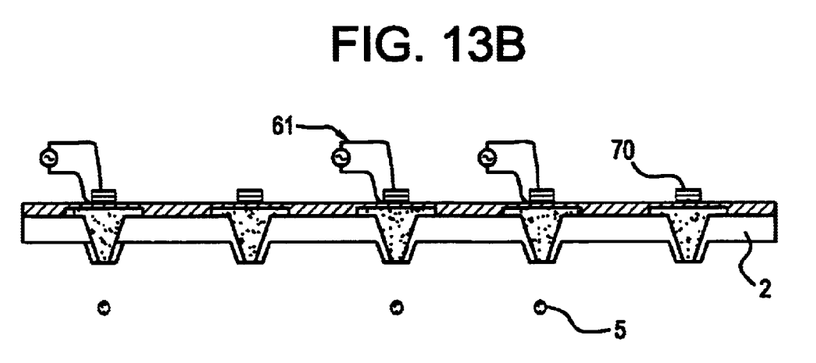

In order to make a selective dispensing of micro-droplets, that is to say that the control is distinctive to each well, the local deformation is carried out by a set of actuating means. FIGS. 13a and 13b illustrate in cross section such a set respectively embodied by electromagnetic means and by piezoelectric means.

The electromagnetic means include a number of electromagnets 60 and a number of magnets 65, disposed in a matrix shape perpendicularly to each well 4, and the piezoelectric means include some piezoelectric chips 70, coupled with excitation circuits 61 of the same type of those used for the electromagnetic means. The piezoelectric trigger of micro-droplets 50 (FIG. 13b) is activated the same way it is activated in the case of electromagnetic triggering (FIGS. 12 et 13a) by the closing the circuits 61, the opening of switches 66 stopping the flow of droplets 50. When using piezoelectric activation devices, the electric signals are in this case of potential differences applied to the terminals of the piezoelectric elements.

The set of actuating means is managed by a control unit 100, see FIG. 3a, programmable through a coupling or multiplexing network, and its implementation is known to man of the art. Such a unit allows to trigger at the same time or successively the suction or the dispensing of a sole reagent or of various reagents through the wells.

It is therefore possible to obtain a high ejection flow of droplets, for instance 100 droplets per second for single well. It is therefore possible to reach the flow of 100 000 for a dispensing head of 1000 wells, with the deforming of the membrane controlled by an outer signal. In fact, the liquid being almost incompressible, the ratio between the travelling speed of the liquid between the upper opening and the ejection opening of the well is inversely proportional to the ratio of the respective surfaces. In the illustrated example, the ratio of the opening sides being about 15, the ejection speed of the droplets is then about 15 times higher than that of the membranes deformation.

Figures 14, 15:
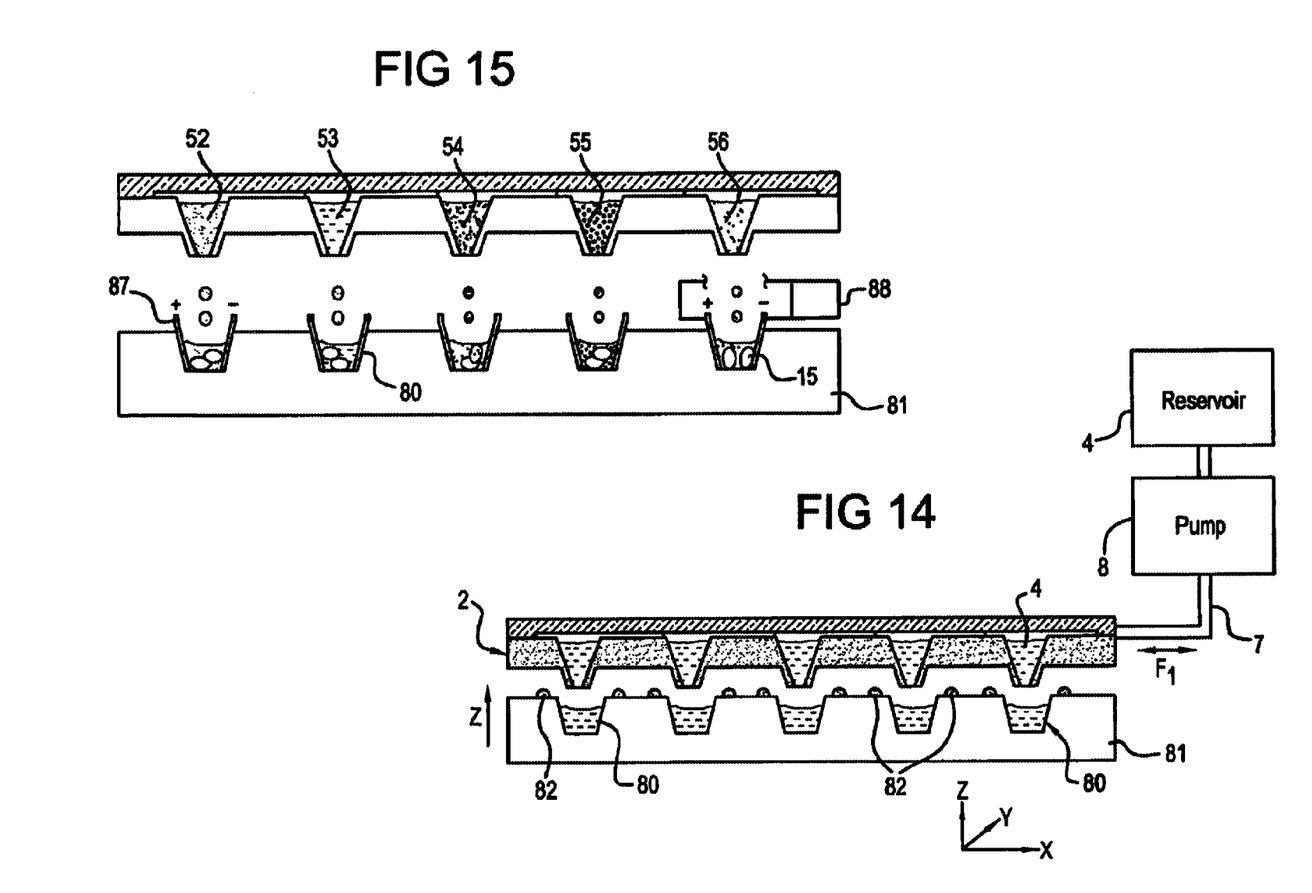
in FIG. 14, a cross section view of a dispensing head in the phase of filling by reagent suction for the preparation of a dispensing cartridge de according to the invention.
in FIG. 15, a cross section view of a dispensing system according to the invention applied to the cell treatment on a titration plate.

For the preparation of a dispensing cartridge according to the invention, reagents are sucked in a dispensing head as shown in the cross section view of FIG. 14. For such a suction to happen, reagents are contained in micro-bowls 80 etched on a plate 81 according to dimensions corresponding to those of well 4. This plate includes in this case 9 600 micro-bowls spaced by 0.6 mm. A few thousands bowls per $cm^2$ can be similarly made, whereas the titration plates presently used generally include only 1 to 4 bowls per $cm^2$.

The plate is moved by micro-metric adjustment (direction Z) towards the substrate 2 until it presses against téflon® waterproof joints 82 fixed to the edges of the micro-bowls 80. Other materials can be alternatively used to form the joints: silicon, vuiton®, polymer, elastomer or adapted thermoplastic materials.

Reagents are then sucked in the wells by the triggering of a pump 8 installed on a draining pipe 7 coupled to the draining ducts of the wells 4, as detailed hereinabove. Plate 81 is also movable according to directions XY in order to enable other suctions from other micro-bowls allowing mixtures of reagents in the same well. The plate is placed on a positioning table XYZ (shown in FIG. 10).

Depending on their applications, the reagents may be of various types: DNAc, oligonucleotides, genes, cells, RNAm, proteins, DNA or RNA sequences amplified by PCR (abbreviated form for <<Polymerisation Chain Reaction>>), antigens et antibodies, therapeutic molecules, serums, etc.

In view of the preparation of probes to manufacture a bio-chip, the deposit of oligonucleotides or of proteins on a titration plate or on a mobile strip is shown in the cross section view of FIG. 15. A dispensing head is fed by the reservoirs and the action of pumps in accordance with FIG. 10. Various therapeutic reagents 52 to 56 are distributed in the wells. Cells to be treated 15 are deposited in the micro-bowls of a titration plate 81. The head and the plate are aligned with precision with the assistance of reference points (not shown). The titration plate is made by injection of a thermoplastic material, such as methyl polymethacrylate or a polycarbonate.

The probes are formed upon the programmed request of the control unit of the activating devices together with the moving of the strip, thus allowing the immediate formation of the probes at the time of this moving: the duration of the formation of the probes 9 is optimised, this allowing to gain a significant amount of time with respect to the formation by successive layers of the prior art. The high flow obtained with the dispensing system according to the invention allows to make probes that can reach, for instance, 60 to 70 nucleotides necessary for the applications in functional genomics and genes expressions. The plate or the strip is moved by micro-metric adjustment according to directions XY to position the ejection openings with the zones to be stamped.

Figure 16:
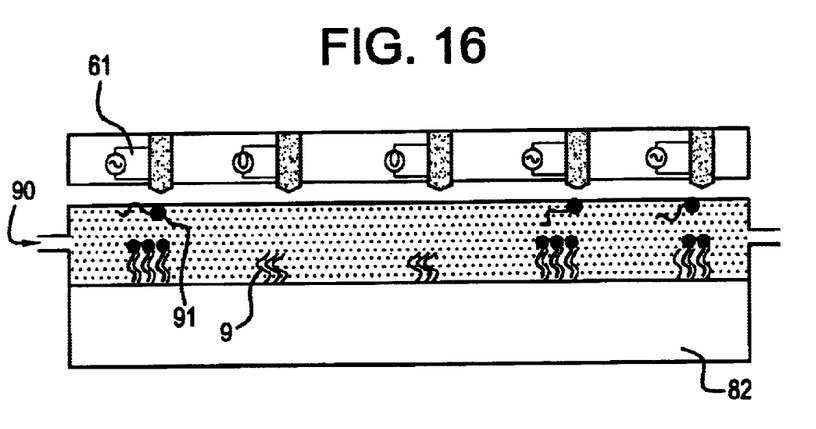
in FIG. 16, a cross section view of a dispensing system according to the invention applied to the detection of hybridisation in a genetic test.

In another example of application to the detection of hybridisation within a genetic test, as shown in cross section in FIG. 16, the strip 82, prepared according to the previous figure, is swept over by DNA flow of a patient 90. The DNA of the patient is previously magnetically marked by grafting of marbles 91, used in the prior art to stop molecules in a magnetic field or, alternately, by fluorescence.

The present solution has the added advantage of re-using the dispensing actuating means to enable the reading of the test by detection, which allows to reduce the quantity of electronic material used, whereas, in the prior art, it is necessary to have reading coils in the titration bowls.

The hybridisation or the immunological interaction allows to fix the DNA of the patient on some of the probes 9. The detection of these hybridisations is made by formation of an induced current in the circuits 61 perpendicularly of the hybridised probes or by optical detection. This detection is made possible by the precision of the probe positioning and by the fact, in the case of magnetic marking, that the same circuits 61 ensure the dispensing of the probes and the detection of the hybridisations.

Figure 17:
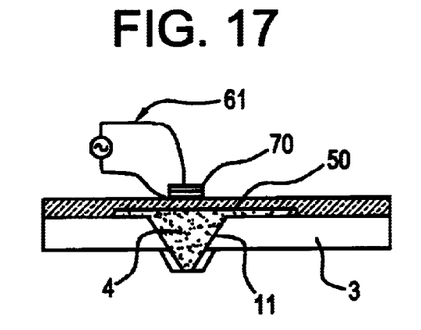
in FIG. 17, a cross section view of a dispensing system according to the invention applied to the percutaneous administration of drugs; and in FIG. 18, a schematic view of the micro-ducts shown in different layers of the membrane.

In the ionto-phoretic application, the percutaneous administration of drugs is carried out, with reference to the cross section view of FIG. 17, from the dispensing head to a dispensing well 4. In this well, a drug is distributed according to the method detailed above. A voltage of a few millivolts is applied by a voltage generating circuit 61 on a piezoelectric cell 70 to deform the membrane 3. A pre-calibrated quantity of drug 50 can then be administered during a given time. Two of the opposing walls 11 of the well can also be polarised to facilitate the absorption of the drug by causing the dilatation of the skin pores.

This invention is not limited to the embodiments described and represented.

It is for instance possible to carry out the configurations of the well, of the actuating means and of the titration bowls otherwise than in a matrix: configurations of concentric circular shape or in spiral are equally suitable.

Figure 18:
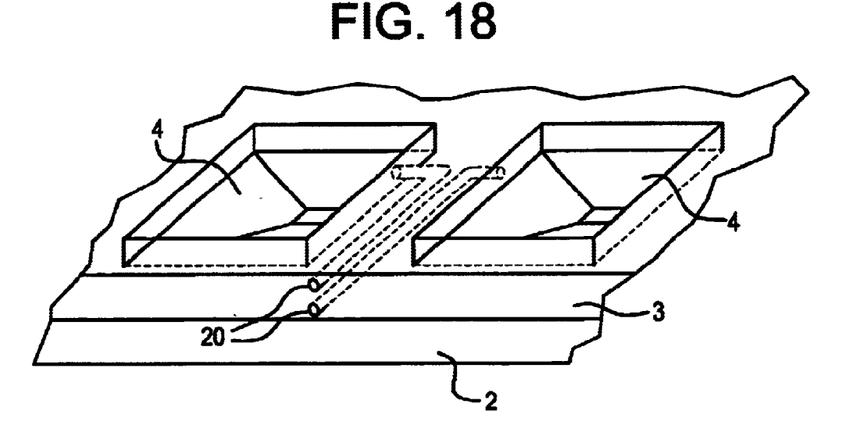

The micro-ducts may either be etched on the substrate or on the membrane. It is possible to make the membrane or the substrate with a multi-layered structure allowing the tridimensional integration of the micro-ducts in different layers. FIG. 18 shows micro-ducts (20) arranged in membrane 3 in different layers, each micro-duct coupled to a respective well (4).

Moreover, it is possible to use other techniques to trigger the local deforming of the membrane, by bimetallic strip effect using thermoelastic or magnetostriction effects: the thermoelastic deformation of a material of the bimetallic strip type disposed to form strips perpendicular to the wells on the membrane. Each strip can be formed by a layer of ferromagnetic material and by a layer of conductive material (in Cu, Al, Au, etc.), the ferromagnetic material being deformed under the effect of a magnetic field created by the electromagnet. It is also possible to use pneumatic means, by electro-vaporisation, or by the application of electrostatic fields.

Moreover, the deforming forces of the membrane or its heating can be created, for instance with the assistance of Foucault currents. Resonating the membrane can be done by deforming the membrane or by vibration of the tip of the duct.

Furthermore, other adaptations are possible to satisfy specific applications. For example, for test cell screening in pharmacology, with reference to FIG. 15, the micro-bowls 80 of a titration plate 81 are equipped with polarized electrodes 87, and means 88 to apply a potential difference to the electrodes in order to generate a polarization in the cell and favor the therapeutical effect on the cells. The cell reactivity test can be optical, that is by fluorescence and/or spectroscopy, or electrical by electrical or electromechanical impedance measurement. It is also possible to apply, inversely, a potential difference of adapted value among these electrodes to generate a polarization in the cells and thus favor the therapeutic effect on the cells.

Another application of the dispensing system according to the invention concerns the dispensing of reagents in the columns of mass spectrometry for the characterisation of the compounds, by parallel or sequential feeding as described above. This application can equally be suitable for chromatographs.

What is claimed is:

1. High-performance dispensing system of micro-droplets, comprising:

a substrate (2);

a membrane covering the substrate; and means (65, 70) for deforming the membrane perpendicularly to cavities (10) formed in the substrate (2), characterized in that the cavities, etched in a material composing the substrate appear in the shape of wells crossing the substrate with a continuous lateral wall (11) of axial symmetry, and in that each well opens on the upper surface and the lower surface of the substrate as respectively a feeding opening (12) and a duct (14) opened as an ejection nozzle (13), the feeding opening presenting an opening higher than the nozzle (13) of the duct, and the duct presenting a shape ratio between 1 and 20;

wherein the wells are configured in one of a matrix form, a circular concentric form, and a spiral form, or combinations thereof; and further comprising a plurality of microducts, the plurality of microducts arranged in layers in three dimensions in either the substrate or membrane, each microduct being coupled to one or more wells by connections perpendicular to the upper openings of the wells.

2. Dispensing system of micro-droplets according to claim 1, wherein the well density reaches 10 000/cm$^2$, with a flow of at least one million droplets per second.

3. Dispensing system of micro-droplets according to claim 1, wherein the means for deforming is managed by a control unit programmable through a multiplexing network to trigger simultaneously or successively the suction or the ejection of identical or different reagents through the wells, by blocks of pre-selected wells or by certain pre-selected wells.

4. Dispensing system of micro-droplets according to claim 1, wherein the material of the substrate or of the membrane is chosen among semiconducting materials, polysilicon, glass, silicon nitrides, ceramics, thermoplastic materials, elastomers, thick photosensitive resins, and electro-formed or electro-eroded metals.

5. Dispensing system of micro-droplets according to claim 1, wherein the membrane is etched to create a network of the micro-ducts to feed the wells, said micro-ducts being coupled at the tip to at least one reagent feeding reservoir.

6. Dispensing system of micro-droplets according to claim 1, wherein the means for locally deforming (65, 70) the membrane (3) are composed of electromagnetic, piezoelectric, magnetostrictive, electrostatic actuators or by electro-evaporation.

7. Dispensing system of micro-droplets according to claim 1, wherein the deformation forces on the membrane are generated by starting a resonance of the membrane (3) or by vibration of the tip of the ducts (14).

8. Dispensing system of micro-droplets according to claim 1, wherein the wells in each line of a matrix configuration are fed by a reservoir through a micro-duct (20) formed in the membrane parallel to the line of wells (10) and coupled laterally to the line or orthogonally to the plane of the substrate (2), the reservoir being etched in the membrane or positioned at a distance and linked to the micro-ducts by flexible connections.

9. Dispensing system of micro-droplets according to claim 1, wherein the matrix form has a number of lines equal to a multiple of four, in order to proceed to the synthesis of probes of DNA from the four mononucleotides (A, C, T, G) for the preparation of bio-chips, and wherein the wells in each line are fed by a reservoir through a micro-duct (32) formed in the membrane (3) parallel to the lines, each reservoir being etched in the membrane or positioned at a distance and linked to the micro-ducts by flexible connections (7).

10. A dispensing cartridge comprising at least a dispensing system according to claim 1, pre-filled with reactants (51), and with titration plates (81) that can show micro-bowls (80) formed one of micro-electronic type etching, manufacturing, molding and thermoforming.

11. The cartridge according to claim 10, wherein the titration plate shows micro-bowls equipped with polarized electrodes for electrical or optical cell reactivity testing.

12. The cartridge according to claim 11, wherein a potential difference is applied between said polarized electrodes in order to generate a polarization in the cell and favor a therapeutical effect on the cells.

13. The cartridge according to claim 10, wherein the membrane is etched to create a network of the micro-ducts to feed the wells, said micro-ducts being coupled at the tip to at least one reagent feeding reservoir.

14. A dispensing kit comprising at least a dispensing system according to claim 1, equipped with at least one aspiration pump (8), and at least one titration plate (81), which can be pre-filled with reagents.

15. The kit according to claim 14, wherein the titration plate shows micro-bowls equipped with polarized electrodes for electrical or optical cell reactivity testing.

16. The kit according to claim 15, wherein a potential difference is applied between said polarized electrodes in order to generate a polarization in the cell and favor a therapeutical effect on the cells.

* * * * *